US006572818B1

(12) United States Patent
Clauzure et al.

(10) Patent No.: US 6,572,818 B1

(45) Date of Patent: Jun. 3, 2003

(54) PROCESS FOR TREATING CORK MATERIAL AND CORK STOPPERS

(75) Inventors: André Clauzure, Evry-les-Chateaux (FR); Patrice Robichon, Chatou (FR)

(73) Assignee: Pernod Ricard, Paris (FR)

( * ) Notice: Subject to any disclaimer, the term of this patent is extended or adjusted under 35 U.S.C. 154(b) by 0 days.

(21) Appl. No.: 09/744,963

(22) PCT Filed: Aug. 11, 1999

(86) PCT No.: PCT/FR99/01968

§ 371 (c)(1),
(2), (4) Date: Feb. 9, 2001

(87) PCT Pub. No.: WO00/09304

PCT Pub. Date: Feb. 24, 2000

(30) Foreign Application Priority Data

Aug. 11, 1998 (FR) ........................................... 98 10288

(51) Int. Cl.[7] ................................................ A61L 2/00

(52) U.S. Cl. .............................. 422/26; 422/5; 422/11; 422/1

(58) Field of Search ................................ 422/5, 11, 26, 422/1; 215/355

(56) References Cited

U.S. PATENT DOCUMENTS 5,174,956 A * 12/1992 Konishi et al. ................ 422/5

FOREIGN PATENT DOCUMENTS

| | | |
|---|---|---|
| DE | 267 733 | 12/1906 |
| EP | 0 395 010 | 10/1990 |
| FR | 343 350 | 8/1904 |

* cited by examiner

*Primary Examiner*—Robert J. Warden, Sr.
*Assistant Examiner*—Sean E. Conley
(74) *Attorney, Agent, or Firm*—Jacobson Holman PLLC

(57) ABSTRACT

The invention concerns a method for treating a cork-based product useful for making stoppers. The invention is characterised in that it comprises the following steps: a) introducing the product in a sealed container; b) subjecting said product to the action of water vapor under pressure ranging between $2.10^5$ and $30.10^5$ Pa for a duration ranging from about 5 seconds to 5 minutes; c) producing an expansion to restore atmospheric pressure inside the container; d) recuperating the treated product.

16 Claims, No Drawings

PROCESS FOR TREATING CORK MATERIAL AND CORK STOPPERS

BACKGROUND OF THE INVENTION

1. Field of the Invention

The present invention relates generally to the manufacture of cork-based stoppers, and more particularly to a process for treating a cork-based product which can be used to make stoppers.

The invention also relates to a stopper comprising this product, for closing bottles of alcoholic or non-alcoholic drinks such as, for example, still or sparkling wines, spirits, ciders and carbonated fruit drinks.

2. Description of the Related Art

The cork from which stoppers are manufactured is a plant tissue produced by the suberophellodermic stratum of cork oak.

It consists of dead cells of alveolar structure. These cells are filled with gas whose composition is very close to that of air.

Cork is composed essentially of about 45% suberin, which is the main constituent of the alveolar cells, about 27% lignin of fibrous structure, which is included in channels or at the surface of the bark, about 12% cellulose and about 17% of various other products such as ceroids, tannins, mineral materials and water.

Cork is a good material for stoppering and storing still or sparkling drinks, in particular wines or other bottled alcohols, since it is a material which is compressible and sufficiently elastic, leaktight and hydrophobic.

Cork contains about 5% water but becomes hydrated slowly.

It is just sufficiently gastight to allow wines or alcohols to age correctly without oxidizing.

However, cork is a natural material which has more or less major defects.

These defects consist mainly of channels with lignified walls or lignin inclusions.

They have a deleterious effect on the elasticity and leaktightness of the stopper.

In addition, they contain substances or precursors thereof which may, during aging, give the stoppered wines or alcohols unpleasant tastes known as "corked tastes".

Several studies have revealed certain substances contained in cork from which stoppers are made, which give rise to adverse changes to wine, giving it a corked taste.

The main substances identified are:

2,4,6-trichloroanisole (TCA), 2,5-dimethylpyrazine, 2-methylthio-3-ethylpyrazine, 4-ethylphenol, 2,6-dichlorophenol, geosmine, guaiacol, 1-octen-3-one, 1-octen-3-ol, 2-methylisobomeol.

These abovementioned substances give wine unacceptable aromas, even at low concentrations.

These substances or precursors thereof are located in the ligneous parts of cork. Thus, the TCA content in cork increases as the proximity to the bark of cork oak (lignified part) increases. Guaiacol is produced by the action of a bacterium on lignin. The other abovementioned substances have as precursors tannins, bacteria or molds which are preferentially in the lignin or the lignified channels.

The conventional process for treating cork for the purpose of manufacturing stoppers comprises a boiling operation carried out on cork sheets or cork barks dried for about 2 years. This operation consists in immersing said cork sheets or barks in a bath of boiling water at a temperature of about 100° C. for about 1 h 30min.

This boiling operation is followed by a rest phase which ranges from 48 hours to three weeks approximately, in particular to stabilize the excess moisture in the treated product.

The cork plates or barks thus treated are then used in the stopper manufacturing line.

Besides the fact that this process for treating cork is very long, the rest phase is a critical step during which the cork may be contaminated with bacteria or molds, which may be the cause of the "corked taste".

In an attempt to eliminate the drawbacks associated with the defects of medium-quality and low-quality natural cork while at the same time maintaining a relatively low cost of manufacture of the stoppers compared with the solution which consists in manufacturing the stoppers using a noble natural cork free of defects, stopper manufacturers have produced agglomerated stoppers consisting of particles of medium-quality or low-quality cork and a binder or adhesive which ensures the cohesion of the stoppers.

Composite stoppers are also known, an example of which is disclosed in patent application FR-A-2 672 002.

Such a stopper consists mainly of a powder of ligneous plant material obtained in particular from cork, expanded plastic microspheres and a food adhesive.

However, although the agglomerated stoppers are cheap to manufacture, their physicochemical and mechanical properties are inferior to those of natural cork stoppers and they therefore cannot be used to store wines or alcohols which are to be aged in bottles.

Furthermore, just as with the abovementioned composite stoppers, the use of agglomerated stoppers does not eliminate the appearance of corked tastes in wines or alcohols bottled and stoppered with such stoppers.

SUMMARY OF THE INVENTION

To overcome the abovementioned drawbacks, the present invention proposes a novel process for treating cork-based products which can be used for making stoppers and which in particular eliminates the risks of appearance of corked tastes in bottled wines or alcohols.

More particularly, the process according to the invention comprises the following steps:

a) said product is placed in a leaktight container, b) said product is subjected to the action of steam at a pressure of between $2\times10^5$ and $30\times10^5$ Pa for a period of between about 5 seconds and 5 minutes, c) a depressurization is carried out to bring the inside of the container to atmospheric pressure, d) the treated product is recovered.

The cork-based products used for this process may be sheets or pieces of cork, intermediate products such as granules, tubing waste, sorting waste or finished products such as stoppers and rejects.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In general, the process in accordance with the invention applies to any cork-based product which may be included in the composition of a stopper.

The process in accordance with the invention makes it possible, within a very short time, to de-aromatize the cork-based product efficiently, in particular by modifying in said product the content of substances listed above which give rise to adverse changes to wine or precursors thereof.

The risks of appearance of corked tastes in alcohols placed in bottles and bottled with stoppers comprising such a treated product are thus eliminated.

In addition, such a process advantageously sterilizes the cork-based product, by destroying the microorganisms contained in this product, which may be precursors of the abovementioned substances that give wines unacceptable flavors.

Depending on the cork-based product treated, the treatment process according to the invention produces cork in different forms.

In particular, according to one embodiment, a slow and gradual depressurization is carried out in step c).

This embodiment is used especially to treat a cork-based product which is already in the form of powder or small granules.

According to another embodiment of the process in accordance with the invention, a sudden, rapid depressurization is carried out in step c).

This is particularly advantageous for obtaining, from a cork-based product which is in the form of large pieces, plates, granules or tubing waste, a treated-cork powder which is ready to be used to make a cork stopper reconstituted using a binder and a filler to give it the desired elasticity.

Such a binder is a food-grade binder such as a polyurethane binder.

This variant of the process may also be used to obtain, from sheets or large pieces of cork, treated granules that are used subsequently in the manufacture of cork stoppers agglomerated using a binder such as a food adhesive.

This advantageously makes it possible to avoid a prior operation of grinding the treated cork-based product.

The treated cork powder thus obtained improves the quality of the sorting and may lead to products that are more enriched in suberin.

According to the invention, dry steam or wet steam may be advantageously used in step b).

The steam pressure used in step b) corresponds to a temperature inside the container of between about 120° C. and 230° C.

Thus, the product contained in the container is penetrated by the steam introduced therein, such that its temperature increases to a temperature of between 120° C. and 230° C., and such that it is softened.

When wet steam is used at the saturating vapor pressure, the moisture content of the cork-based product treated is increased.

When superheated dry steam is used, the moisture content of the cork-based product treated is not modified.

In accordance with the process according to the invention, the steam is introduced under pressure into the container in step b).

This may advantageously be carried out by creating a flow of steam inside the container.

Needless to say, the steam may be introduced into the container without creating a flow.

Step b) preferably lasts between 30 seconds and one minute.

Moreover, it may be envisaged in step b) to heat the container containing the product and water, for a treatment with wet steam.

It may also be chosen to heat the product directly by introducing superheated dry steam.

The invention also proposes a stopper for closing bottles of still or sparkling alcoholic drinks or carbonated drinks, which comprises a cork-based product treated using the abovementioned process.

By way of example, cork granules free of defects were contaminated with trichloroanisole and were treated using the process according to the invention.

The contaminated granules have a characteristic corked-taste odor (moldy, earthy). These granules were subjected to the action of steam under a pressure equal to $20\times10^5$ Pa for one minute followed by a sudden depressurization.

A cork powder was thus recovered directly at the outlet of the container.

The product was then analyzed by sensory and chemical analysis.

For the purpose of the sensory analysis, the cork powder treated according to *the process in accordance with the invention was macerated (10 g/l) in a 20 vol % aqueous-alcoholic solution for 48 hours.

Once filtered, the solutions obtained were given to tasters.

The tasters were asked to place the solutions on a scale from 0 to 10 as a function of their TCA content (strong odor of TCA=10).

The tasters are provided with two references:

a control glass free of TCA and a control glass contaminated with TCA.

Table 1 summarizes the average grades obtained out of 10.

TABLE 1

| | A1: non-contaminated, untreated cork | A2: non-contaminated, treated cork | B1: contaminated, untreated cork | B2: contaminated, treated cork |
|---|---|---|---|---|
| TCA intensity | 1.1 | 2.3 | 7** | 2.3 |

**means the 1% threshold (L.S.D. test)

The results of the sensory analysis which are given in Table 1 show the efficacy of the process according to the invention.

After treatment, the non-contaminated cork (sample A2) suffered a change in its aroma, but the grade obtained shows that the TCA intensity remains entirely acceptable.

The change in aroma between the non-contaminated, untreated cork (sample A1) and the non-contaminated, treated cork (sample A2) is not significant.

On the other hand, after treatment on the contaminated cork (sample B1 becoming sample B2), the tasters no longer detect the characteristic odor of TCA.

For the purpose of the chemical analysis, the cork powder treated according to the process in accordance with the invention is introduced into 96 vol % alcohol at a concentration of 5 g/11 ml.

After macerating for 48 hours, the solutions are filtered and analyzed by GCPMS.

The detection threshold is 5 picograms/micro-liter.

The results of the chemical analysis are given in Table 2.

TABLE 2

| | A1: non-contaminated, untreated cork | A2: non-contaminated, treated cork | B1: contaminated, untreated cork | B2: contaminated, treated cork |
|---|---|---|---|---|
| Residual TCA in ppb | 0 | 0 | 32 | 0 |

The chemical analyses performed on the treated cork powder confirm the abovementioned sensory analysis results.

Only the solution obtained from B1 has a residual TCA peak.

No TCA was detected in the solution obtained from B2.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A process for treating a cork-based product which can be used for making stoppers, comprising the following steps:

a) placing said product inside a leaktight container;

b) subjecting said product to the action of steam at a temperature of between 120 ° C. and 230° C. and at a pressure of between $2\times10^5$ and $30\times10^5$ Pa for a period of between about 5 seconds and 5 minutes without creating a steam flow in said container;

c) carrying out a sudden, rapid depressurization to bring the inside of the container to atmospheric pressure; and d) recovering a treated-cork powder.

2. A process for treating a cork-based product which can be used for making stoppers, comprising the following steps:

a) placing said product inside a leaktight container;

b) subjecting said product in said container to the action of steam at a pressure of between $2\times10^5$ and $30\times10^5$ Pa for a period of between about 5 seconds and 5 minutes without creating a steam flow through said container;

c) carrying out a sudden, rapid depressurization to bring the inside of the container to atmospheric pressure; and d) recovering as a result of step c) treated cork granules ready to be used to make cork stopper without requiring a prior operation of grinding.

3. The process according to claim 1, wherein the steam is a dry steam.

4. The process according to claim 1, wherein the steam is a wet steam.

5. The process according to claim 1, wherein step b) lasts between 30 seconds and 1 minute.

6. The process according to claim 1, wherein, in step b), the steam is introduced under pressure into the container.

7. The process according to claim 6, wherein, in step b), the container containing the product and water is heated.

8. Use of a cork-based product treated using the process according to claim 1 to produce a stopper for closing bottles of still or sparkling alcoholic drinks or carbonated drinks.

9. The process according to claim 1, wherein the temperature during step b) is above 130° C.

10. The process according to claim 2, wherein a temperature during step b) can be as high as 230° C.

11. The process according to claim 2, wherein the steam is a dry steam.

12. The process according to claim 2, wherein the steam is a wet steam.

13. The process according to claim 2, wherein step b) lasts between 30 seconds and 1 minute.

14. The process according to claim 2, wherein, in step b), the container containing the product and water is heated.

15. The process according to claim 1, wherein step b) is conducted at a pressure of from at least $20\times10^5$ Pa to $30\times10^5$ Pa.

16. The process according to claim 2, wherein step b) is conducted at a pressure of at least $20\times10^5$ Pa to $30\times10^5$ Pa.

* * * * *